United States Patent
Wu et al.

(10) Patent No.: US 11,315,350 B2
(45) Date of Patent: Apr. 26, 2022

(54) METHOD FOR ASSESSING DRIVER FATIGUE

(71) Applicant: NATIONAL CHIAO TUNG UNIVERSITY, Hsinchu (TW)

(72) Inventors: Bing-Fei Wu, Hsinchu (TW); Kuan-Hung Chen, Hsinchu (TW); Po-Wei Huang, Douliu (TW); Yin-Cheng Tsai, Taoyuan (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 358 days.

(21) Appl. No.: 16/559,358

(22) Filed: Sep. 3, 2019

(65) Prior Publication Data
US 2020/0320319 A1    Oct. 8, 2020

(30) Foreign Application Priority Data
Apr. 8, 2019    (TW) ................... 108112128

(51) Int. Cl.
*G06K 9/00* (2022.01)
*G06V 20/59* (2022.01)
(Continued)

(52) U.S. Cl.
CPC ........ *G06V 20/597* (2022.01); *A61B 5/02416* (2013.01); *A61B 5/165* (2013.01);
(Continued)

(58) Field of Classification Search
CPC ........... G06K 9/00845; G06K 9/00315; G06K 9/00832; A61B 5/02416; A61B 5/165;
(Continued)

(56) References Cited

U.S. PATENT DOCUMENTS

| 8,725,311 B1 * | 5/2014 | Breed ...................... A61B 5/11 701/1 |
| 10,328,946 B2 * | 6/2019 | Brooks ................. B60W 50/14 |

(Continued)

FOREIGN PATENT DOCUMENTS

| CN | 103824420 | * 12/2013 |
| CN | 103824420 A | 5/2014 |
| CN | 105719431 A | 6/2016 |

OTHER PUBLICATIONS

Huang et al., "Image based contactless blood pressure assessment using pulse transit time", published in 2017 IEEE, International Automatic Control Conference (CACS), 2017, 6 pages.
(Continued)

*Primary Examiner* — Avinash Yentrapati
(74) *Attorney, Agent, or Firm* — Womble Bond Dickinson (US) LLP

(57) ABSTRACT

A method for assessing driver fatigue is implemented by a processor and includes steps of: based on images of a driver captured by an image capturing device, obtaining an entry of physiological information that indicates a physiological state of the driver; based on one of the images of the driver, obtaining an entry of facial expression information that indicates an emotional state of the driver; based on one of the images of the driver, obtaining an entry of behavioral information that indicates driver behavior of the driver; and based on the entry of physiological information, the entry of facial expression information and the entry of behavioral information, obtaining a fatigue score that indicates a level of fatigue of the driver.

6 Claims, 11 Drawing Sheets

(51) Int. Cl.
*A61B 5/024* (2006.01)
*A61B 5/18* (2006.01)
*A61B 5/00* (2006.01)
*A61B 5/16* (2006.01)
*G06V 40/16* (2022.01)
*B60Q 9/00* (2006.01)

(52) U.S. Cl.
CPC .............. *A61B 5/18* (2013.01); *A61B 5/6893* (2013.01); *A61B 5/7264* (2013.01); *G06V 40/176* (2022.01); *A61B 5/0002* (2013.01); *A61B 5/0077* (2013.01); *A61B 2576/00* (2013.01); *B60Q 9/00* (2013.01)

(58) Field of Classification Search
CPC ....... A61B 5/18; A61B 5/6893; A61B 5/7264; A61B 5/0002; A61B 5/0077; A61B 2576/00; B60Q 9/00; G06T 2207/30248; G06T 2207/30268
See application file for complete search history.

(56) References Cited

U.S. PATENT DOCUMENTS

| | | | |
|---|---|---|---|
| 11,065,958 B2* | 7/2021 | Mestha | G06V 40/168 |
| 2008/0238694 A1* | 10/2008 | Ishida | A61B 5/163 |
| | | | 340/575 |
| 2011/0077548 A1* | 3/2011 | Torch | A61B 5/165 |
| | | | 600/558 |
| 2014/0276090 A1* | 9/2014 | Breed | A61B 5/02433 |
| | | | 600/473 |
| 2016/0001781 A1* | 1/2016 | Fung | B60K 28/02 |
| | | | 701/36 |
| 2018/0186234 A1* | 7/2018 | Mestha | H04N 7/181 |
| 2018/0186379 A1* | 7/2018 | Brooks | B60W 50/082 |
| 2018/0360387 A1* | 12/2018 | Bulut | G06T 7/70 |
| 2019/0077409 A1* | 3/2019 | Zandi | G06V 20/597 |
| 2019/0083022 A1* | 3/2019 | Huang | A61B 5/6824 |

OTHER PUBLICATIONS

Wu et al., "Adaptive Feature Mapping For Customizing Deep Learning Based Facial Expression Recognition Model," IEEE Access, vol. 6, 2018, 11 pages.

* cited by examiner

METHOD FOR ASSESSING DRIVER FATIGUE

CROSS-REFERENCE TO RELATED APPLICATION

This application claims priority of Taiwanese Invention Patent Application No. 108112128, filed on Apr. 8, 2019.

FIELD

The disclosure relates to a method of image processing on a vehicle, and more particularly to a method for assessing driver fatigue.

BACKGROUND

Conventionally, a determination as to whether a driver is fatigued, which is a condition that concerns traffic safety, is made based on body movements or facial movements of the driver that are interpreted by performing image processing on images of the driver. However, aspect of physiological conditions of the driver is not taken into account, so accuracy of the determination made by using the conventional method is often less than ideal.

SUMMARY

Therefore, an object of the disclosure is to provide a method for assessing driver fatigue that can alleviate at least one of the drawbacks of the prior art.

According to the disclosure, the method is to be implemented by a processor. The processor is electrically connected to an image capturing device. The image capturing device continuously captures a plurality of images of a driver. The method includes steps of:

(A) based on the images of the driver captured by the image capturing device, obtaining an entry of physiological information that indicates a physiological state of the driver;

(B) based on one of the images of the driver, obtaining an entry of facial expression information that indicates an emotional state of the driver;

(C) based on one of the images of the driver, obtaining an entry of behavioral information that indicates driver behavior of the driver; and (D) based on the entry of physiological information, the entry of facial expression information and the entry of behavioral information, obtaining a fatigue score that indicates a level of fatigue of the driver.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
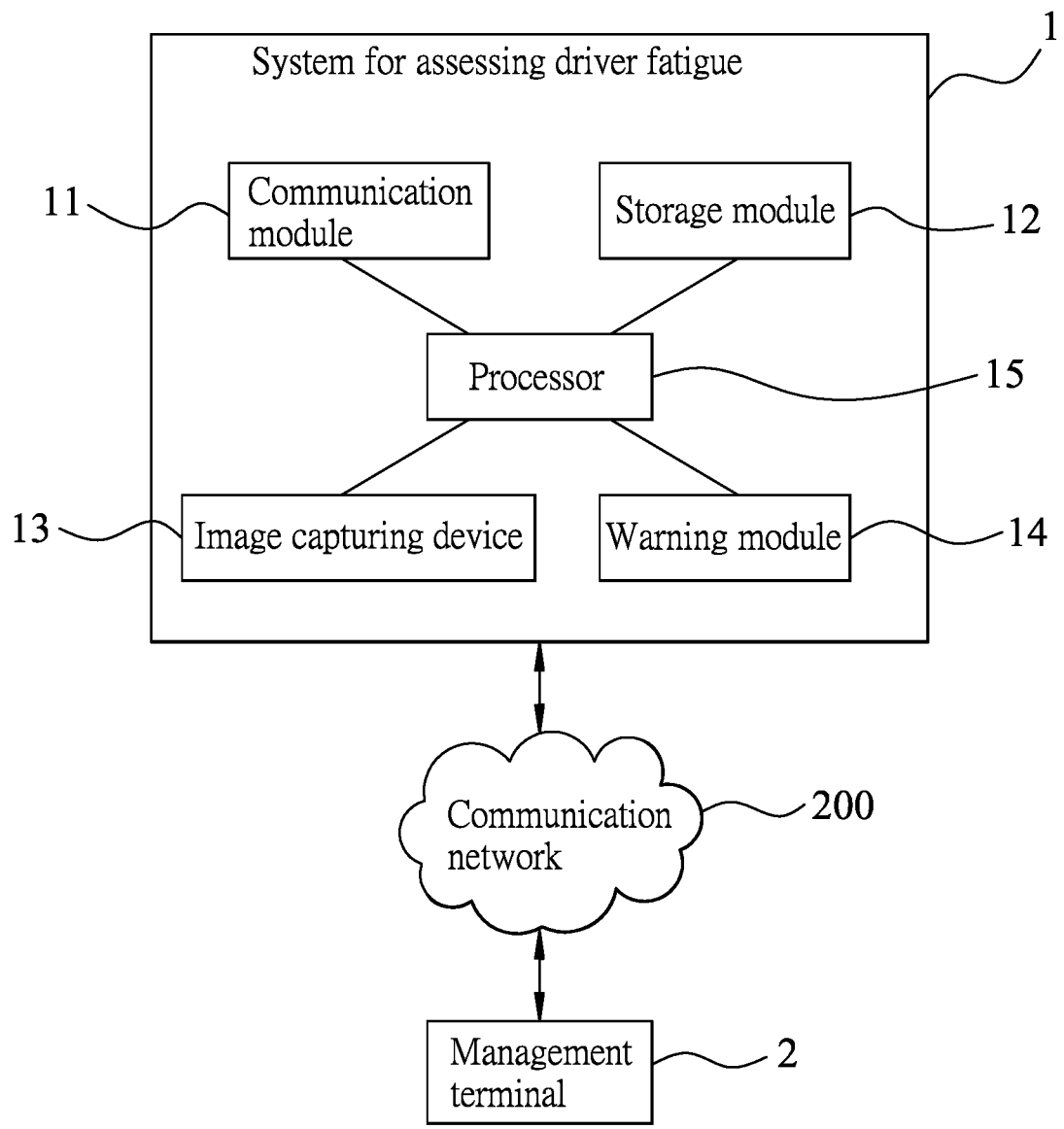
FIG. 1 is a block diagram illustrating an embodiment of a system for assessing driver fatigue that implements a method for assessing driver fatigue according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an embodiment of a system 1 for assessing driver fatigue that implements a method for assessing driver fatigue according to the disclosure is illustrated. The system 1 is connected to a management terminal 2 via a communication network 200.

The system 1 includes a communication module 11 that is able to communicate with the management terminal 2 via the communication network 200, a storage module 12, an image capturing device 13, a warning module 14, and a processor 15 that is electrically connected to the communication module 11, the storage module 12, the image capturing device 13 and the warning module 14.

In this embodiment, the communication module 11 is implemented to be a wireless transceiver that supports wireless communication standards such as Bluetooth technology standards or cellular network technology standards, but is not limited thereto.

The storage module 12 is configured to store a plurality of classification models that are trained by performing one of supervised classification and unsupervised classification (e.g., algorithms of neural networks, but not limited thereto) on a plurality of predetermined learning samples. In this embodiment, the classification models include a classification model for fatigue level assessment, a predetermined classification model of facial expression and a predetermined classification model of driver behavior. In addition, the storage module 12 is further configured to store a fuzzy model that is trained according to predetermined learning samples corresponding to different physiological information.

In this embodiment, the storage module 12 may be implemented by flash memory, a hard disk drive (HDD) or a solid state disk (SSD), an electrically-erasable programmable read-only memory (EEPROM) or any other non-volatile memory devices, but is not limited thereto.

The image capturing device 13 is configured to continuously capture a plurality of images of a driver. In one embodiment, the image capturing device 13 is implemented to be an infrared camera, and the images of the driver may be implemented to be infrared (IR) images. However, implementation of the image capturing device 13 is not limited to such and may vary in other embodiments. For example, the image capturing device 13 may be a digital video camera or an IR video camera.

In this embodiment, the warning module 14 may be implemented to be a speaker or a warning light, but implementation of the warning module 14 is not limited to the disclosure herein and may vary in other embodiments.

In this embodiment, the processor 15 may be implemented by a central processing unit (CPU), a microprocessor or any circuit configurable/programmable in a software manner and/or hardware manner to implement functionalities described in this disclosure. However, implementation of the processor 15 is not limited to the disclosure herein and may vary in other embodiments.

In this embodiment, the management terminal 2 may be implemented to be a personal computer, a data server or a cloud server, but implementation thereof is not limited to what are disclosed herein and may vary in other embodiments.

Figure 2:
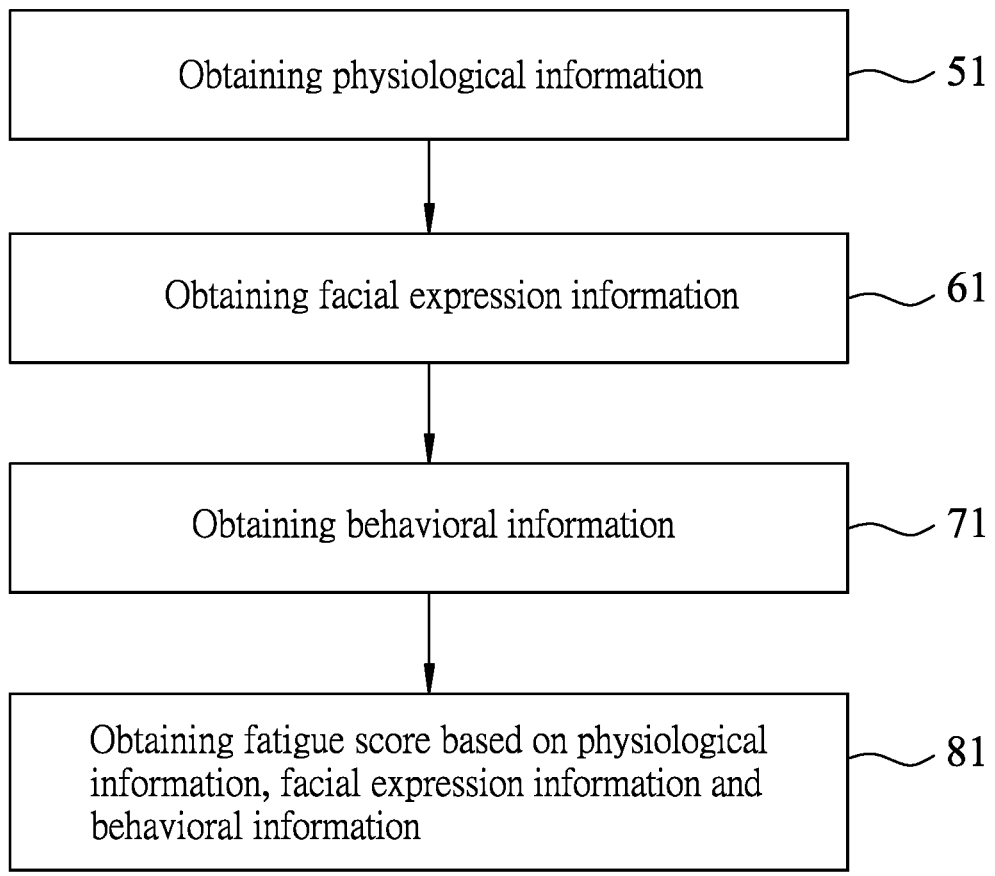
FIG. 2 is a flow chart illustrating an embodiment of the method for assessing driver fatigue according to the disclosure.

Referring to FIG. 2, the method for assessing driver fatigue according to the disclosure includes a procedure of obtaining an entry of physiological information, a procedure of obtaining an entry of facial expression information, a procedure of obtaining an entry of behavioral information and a procedure of obtaining a fatigue score that respectively correspond to steps 51, 61, 71 and 81 described as follows. It should be noted that in some embodiments, the method further includes a procedure of warning the driver.

In step 51, based on the images of the driver captured by the image capturing device 13, the processor 15 obtains the entry of physiological information that indicates a physiological state of the driver.

The entry of physiological information includes at least one of the following members: a heart rate that is a number of heartbeats of the driver per unit of time; a standard deviation of normal-to-normal intervals (SDNN) of a sinus rhythm that is associated with the heartbeat of the driver; a ratio of low frequency power to high frequency power (LF/HF ratio) that is associated with sympathovagal balance of the driver; a respiratory rate that is a number of breaths of the driver per unit of time; and a blood pressure reading. In one embodiment, the entry of physiological information may be in time domain, and exemplarily includes the following three members: a heart rate; an SDNN; and a blood pressure reading. In one embodiment, the entry of physiological information is in frequency domain and exemplarily includes the following three members: a heart rate; an LF/HF ratio; and a respiratory rate.

In step 61, based on one of the images of the driver, the processor 15 obtains the entry of facial expression information that indicates an emotional state of the driver.

In step 71, based on one of the images of the driver, the processor 15 obtains the entry of behavioral information that indicates driver behavior of the driver. The entry of behavioral information includes at least one of an assessment of eye fatigue, an assessment of a first sign of fatigue, an assessment of a second sign of fatigue, or an assessment of a third sign of fatigue.

In step 81, based on at least one of the entry of physiological information, the entry of facial expression information or the entry of behavioral information, the processor 15 obtains the fatigue score that indicates a level of fatigue of the driver by using the classification model for fatigue level assessment that has been trained by, for example, algorithms of neural networks.

Specifically speaking, for each member of the entry of physiological information, based on said member and a fuzzy model that is associated with said member, the processor 15 obtains a corresponding score. Then, the processor 15 obtains the fatigue score by using the classification model for fatigue level assessment that has been trained by supervised classification or unsupervised classification (e.g., algorithms of neural networks). For example, based on the heart rate of the entry of physiological information and a fuzzy model that is associated with heart rate, the processor 15 obtains a heart-rate score that is associated with the driver; based on the SDNN of the entry of physiological information and a fuzzy model that is associated with SDNN, the processor 15 obtains an SDNN score that is associated with the driver; and based on the LF/HF ratio of the entry of physiological information and a fuzzy model that is associated with LF/HF ratio, the processor 15 obtains an LF/HF-ratio score that is associated with the driver. In one embodiment, the processor 15 obtains the fatigue score that indicates the level of fatigue of the driver based on the heart-rate score, the SDNN score and the LF/HF-ratio score by using the classification model for fatigue level assessment, in which case the classification model for fatigue level assessment is associated with heart rate, SDNN, LF/HF-ratio, facial expression information and behavioral information.

It is worth noting that the fuzzy model that is associated with a member of the entry of physiological information is implemented by a Gaussian mixed model (GMM) which serves as a membership function, and is utilized to obtain the score that corresponds to the member of the entry of physiological information. In other embodiments, the fatigue score is obtained by performing defuzzification on a result of supervised classification or unsupervised classification.

Since implementations of GMM, fuzzy model, defuzzification, supervised classification and unsupervised classification (e.g., algorithms of neural networks) are well known to one skilled in the relevant art, detailed explanations of the same are omitted herein for the sake of brevity.

In one embodiment, the processor 15 obtains the fatigue score based only on the entry of physiological information. That is to say, in such embodiment, the classification model for fatigue level assessment is trained by unsupervised classification (e.g., algorithms of neural networks, but not limited thereto) with training data that is associated with physiological information. For example, when the entry of physiological information includes the heart rate and the SDNN, the classification model for fatigue level assessment is trained with training data that is associated with heart rate and SDNN. When the entry of physiological information simply includes the LF/HF ratio, the classification model for fatigue level assessment is trained with training data that is associated with LF/HF ratio.

In one embodiment, the processor 15 obtains the fatigue score based on the entry of physiological information and the entry of facial expression information. In this embodiment, the classification model for fatigue level assessment is trained by unsupervised classification (e.g., algorithms of neural networks, but not limited thereto) with training data that is associated with physiological information and facial expression information.

In one embodiment, the processor 15 obtains the fatigue score based on the entry of physiological information, the entry of facial expression information and the entry of behavioral information. In this embodiment, the classification model for fatigue level assessment is trained by unsupervised classification (e.g., algorithms of neural networks, but not limited thereto) with training data that is associated with physiological information, facial expression information and behavioral information.

In one embodiment, the processor 15 determines whether the fatigue score is greater than a fatigue threshold, and when it is determined that the fatigue score is greater than the fatigue threshold, generates a warning message and transmits the warning message to the warning device 14 so as to notify the driver of the need to take a rest.

In one embodiment, the processor 15 transmits the entry of physiological information, the entry of facial expression information, the entry of behavioral information and the fatigue score via the communication module 11 to the management terminal 2 for monitoring, controlling, recording and analyzing driving conditions of the driver based on the received data.

Figure 3:
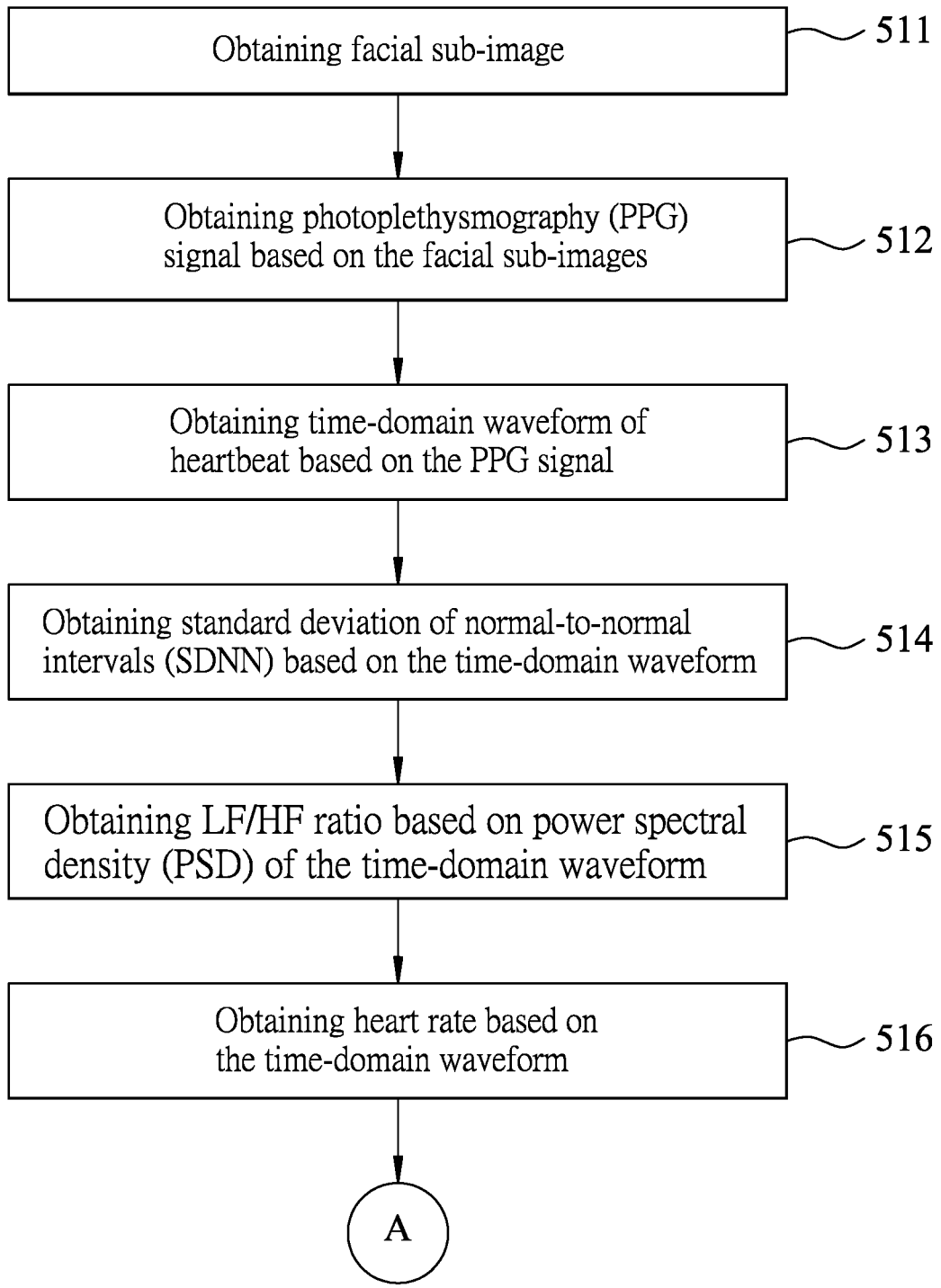
FIGS. 3 and 4 cooperatively constitute a flow chart for illustrating an embodiment of a procedure of obtaining an entry of physiological information in the method for assessing driver fatigue according to the disclosure.
Figure 4:
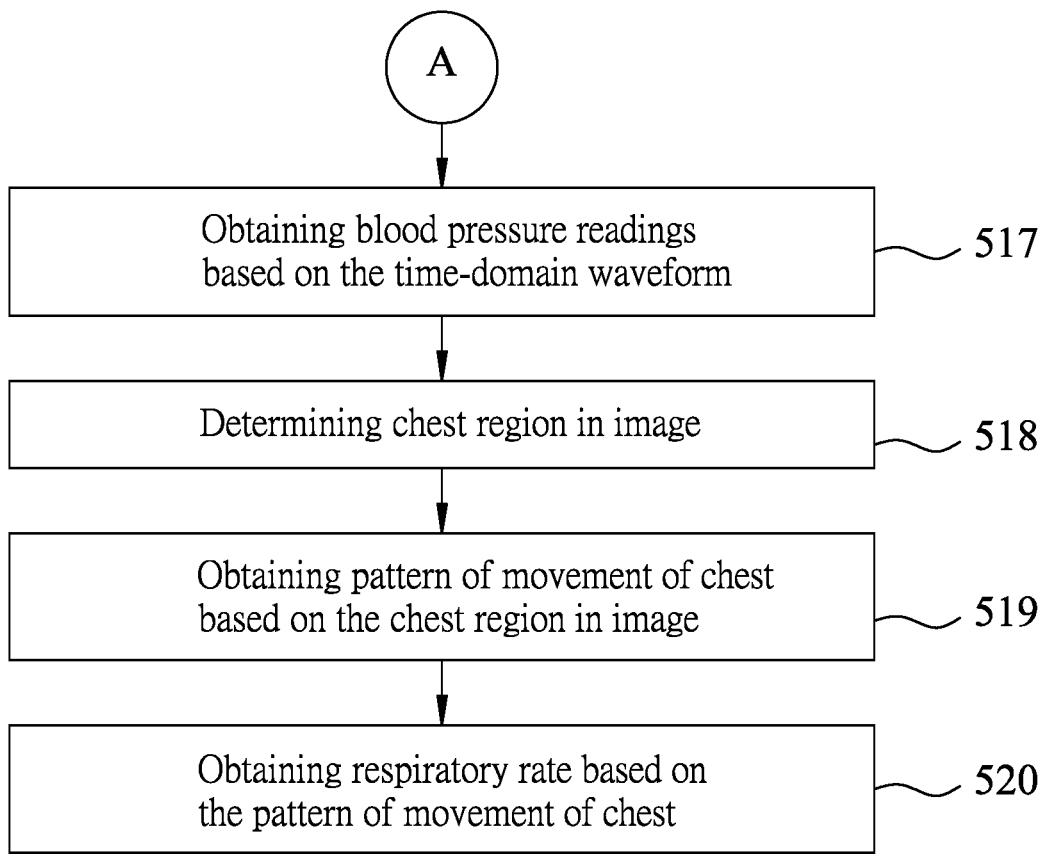

Referring to FIGS. 3 and 4, step 51 further includes sub-steps 511 to 520 described as follows.

In sub-step 511, for each of the images, based on the image, the processor 15 obtains a facial sub-image that corresponds to a facial region of the driver in the image. In this embodiment, the facial region is a cheek region. It is worth to note that in this embodiment, the processor 15 converts the facial sub-image into a grayscale image, and averages all pixel values of the grayscale image so as to generate an average grayscale value that corresponds to the facial sub-image. When the facial sub-image is encoded by an RGB color model, a pixel of the facial sub-image has an RGB triplet (R, G, B), where R represents a red color value, G represents a green color value and B represents a blue color value. The pixel value of a pixel of the grayscale image is calculated as a normalized weighted sum of components of the RGB triplets, e.g., R*0.299+G*0.587+B*0.114. However, implementation of the grayscale image is not limited to the disclosure herein and may vary in other embodiments. In a scenario where the image is an IR image, the RGB triplets of the facial sub-image and the pixel values of the grayscale image can be adjusted based on demands and characteristics of the image.

In sub-step 512, based on the average grayscale values that correspond to the facial sub-images for all the images, the processor 15 obtains a photoplethysmography (PPG) signal that is associated with heartbeat of the driver. Since implementation of obtaining the PPG is well known to one skilled in the relevant art, detailed explanation of the same is omitted herein for the sake of brevity.

In sub-step 513, based on the PPG signal, the processor 15 obtains a time-domain waveform that is associated with heartbeat of the driver. Specifically speaking, heartbeat of the driver cause variations in blood volume beneath the skin of the facial region of the driver, resulting in variations in color of the facial sub-images thus obtained. Therefore, variation in heartbeat of the driver, i.e., the time-domain waveform associated with heartbeat of the driver, can be obtained based on variation in the average grayscale value corresponding to the facial sub-images.

In sub-step 514, based on the time-domain waveform obtained in sub-step 513, the processor 15 obtains the SDNN. Specifically speaking, the processor 15 removes tiny peaks, which may be noise, from the time-domain waveform at first, and then obtains inter-peak intervals of the time-domain waveform. After that, the processor 15 obtains the SDNN based on the inter-peak intervals of the time-domain waveform.

In sub-step 515, the processor 15 obtains the LF/HF ratio based on a power spectral density (PSD) of the time-domain waveform, where the PSD is in frequency domain and is calculated by performing Lomb-Scargle periodogram, which is an implementation of Fourier transform, on the time-domain waveform obtained in sub-step 513. In this embodiment, the low frequency power corresponds to a variance of intervals of regular heartbeats within a low frequency range of between 0.04 and 0.15 Hz, and is calculated by taking an integral of the PSD over an interval defined by 0.04 Hz and 0.15 Hz; the high frequency power corresponds to a variance of intervals of regular heartbeats within a high frequency range of between 0.15 and 0.4 Hz, and is calculated by taking another integral of the PSD over an interval defined by 0.15 Hz and 0.4 Hz. Since implementation of obtaining the PSD by Lomb-Scargle periodogram is well known to one skilled in the relevant art, detailed explanation of the same is omitted herein for the sake of brevity.

In sub-step 516, based on the time-domain waveform obtained in sub-step 513, the processor 15 obtains the heart rate. Specifically speaking, the processor 15 counts a number of heartbeats of the driver in a predetermined time interval based on the time-domain waveform, and then derives a number of heartbeats of the driver per minute based on the number of heartbeats of the driver in the predetermined time interval. In one embodiment, the heart rate is obtained by analyzing a spectrum which is established by performing Fourier transform on the time-domain waveform, which is a distribution of frequency components of the time-domain waveform, and which contains heart rate information. One of the frequency components that corresponds to the maximum magnitude of the spectrum is recognized as the heart rate. Since implementation of obtaining the heart rate by Fourier transform is well known to one skilled in the relevant art, detailed explanation of the same is omitted herein for the sake of brevity.

In sub-step 517, based on the time-domain waveform obtained in sub-step 513, the processor 15 obtains the blood pressure readings in regard to both systolic pressure and diastolic pressure. It should be noted that details of implementations of sub-steps 511 to 513 and 517 can be understood by referring to Huang, Po-wei et al., "Image based contactless blood pressure assessment using pulse transit time", published in 2017 IEEE International Automatic Control Conference (CACS), but is not limited thereto.

In sub-step 518, for each of the images, based on the image, the processor 15 determines a chest region of the driver in the image.

Figure 5:
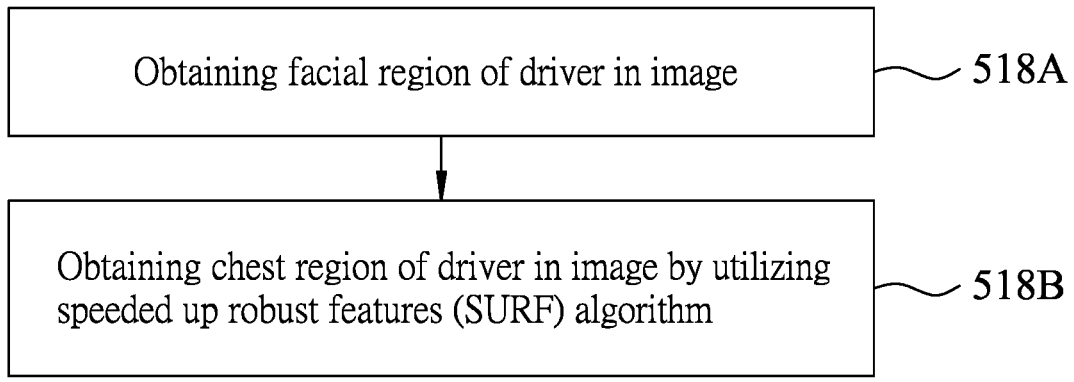
FIG. 5 is a flow chart illustrating an embodiment of a sub-procedure of determining a chest region of the driver in the image in the method for assessing driver fatigue according to the disclosure.

Referring to FIG. 5, sub-step 518 further includes a sub-step 518A and a sub-step 518B.

In sub-step 518A, for each of the images, based on the image, the processor 15 determines the facial region of the driver in the image.

In sub-step 518B, for each of the images, based on the facial region of the driver in the image thus determined, the processor 15 utilizes a speeded up robust features (SURF) algorithm to determine the chest region of the driver in the image. Since implementation of the SURF algorithm is well known to one skilled in the relevant art, detailed explanation of the same is omitted herein for the sake of brevity.

In sub-step 519, based on the chest region of the driver in the image thus obtained, the processor 15 utilizes an optical flow method to obtain a pattern of movement of a chest in another predetermined time interval. Since implementation of the optical flow method is well known to one skilled in the relevant art, detailed explanation of the same is omitted herein for the sake of brevity.

In sub-step 520, based on the pattern of movement of the chest in said another predetermined time interval thus obtained, the processor 15 obtains another time-domain waveform that is associated with breathing of the driver, and the processor 15 performs Fourier transform on said another time-domain waveform so as to result in another spectrum which is a distribution of frequency components of said another time-domain waveform. Thereafter, the processor 15 obtains the respiratory rate by determining one of the frequency components that corresponds to the maximum magnitude of said another spectrum to serve as the respiration rate.

Figure 6:
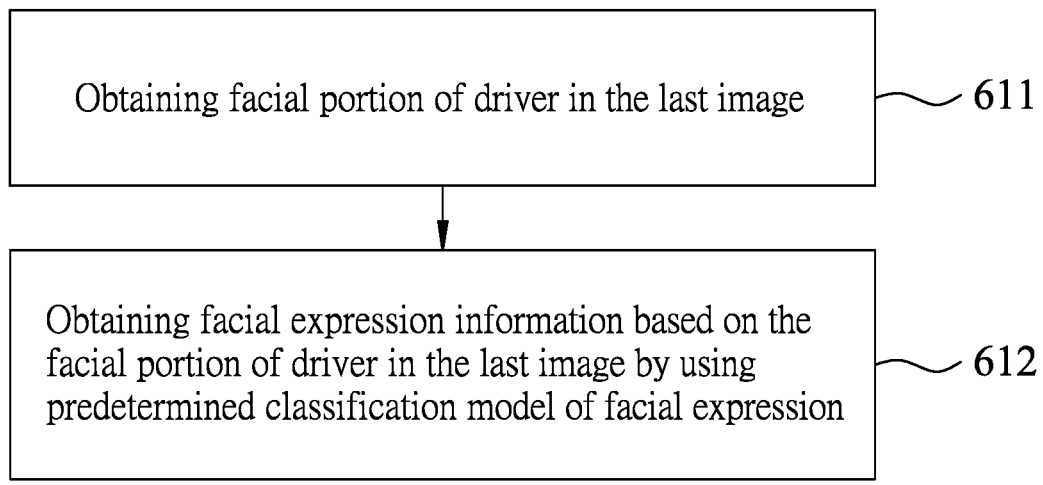
FIG. 6 is a flow chart illustrating an embodiment of a procedure of obtaining an entry of facial expression information in the method for assessing driver fatigue according to the disclosure.

Referring to FIG. 6, step 61 further includes sub-steps 611 and 612 described as follows.

In sub-step 611, based on a last one (as of now) of the images of the driver captured by the image capturing device 13, the processor 15 obtains a facial portion of the driver in the last one of the images.

In sub-step 612, based on the facial portion of the driver in the last one of the images by using a predetermined classification model of facial expression, the processor 15 obtains the entry of facial expression information that corresponds to the facial expression of the driver in the last one of the images and that includes an anger score, a disgust score, a scare score, a happiness score, a sadness score and an amazement score. It should be noted that details of implementations of obtaining the entry of facial expression information can be understood by referring to Wu, Bing-fei et al., "Adaptive feature mapping for customizing deep learning based facial expression recognition model", published Feb. 14, 2018 in IEEE Access, Volume 6, but is not limited thereto.

Figure 7:
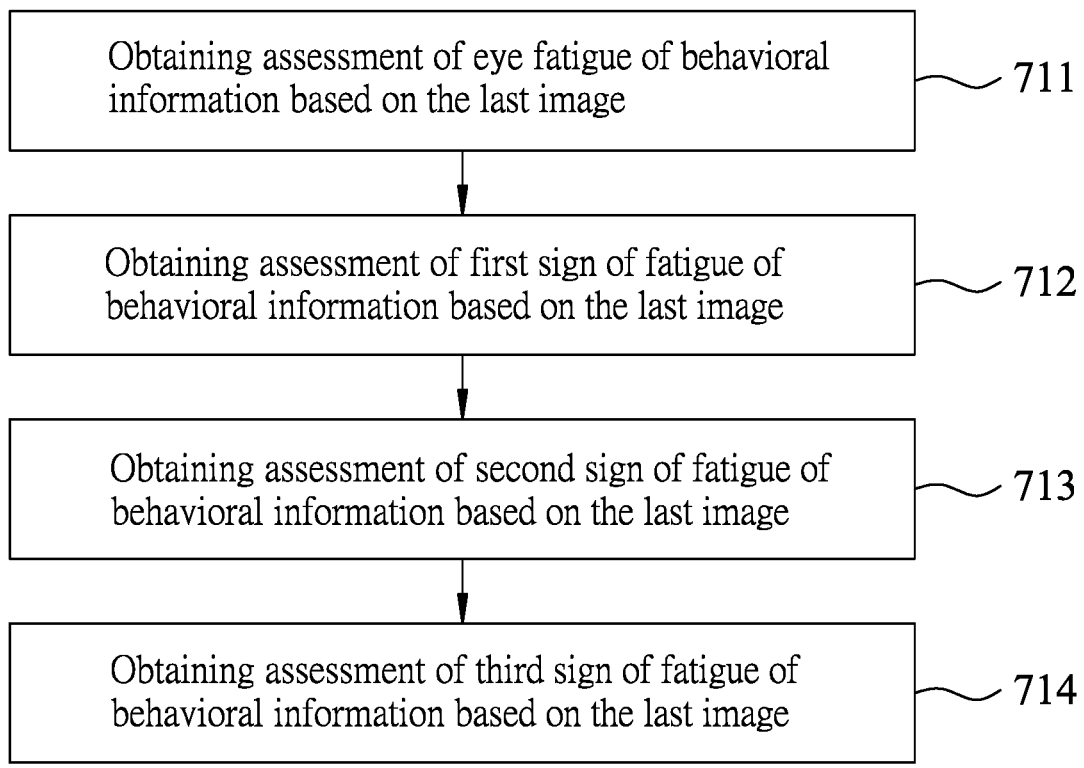
FIG. 7 is a flow chart illustrating an embodiment of a procedure of obtaining an entry of behavioral information in the method for assessing driver fatigue according to the disclosure.

Referring to FIG. 7, step 71 further includes sub-steps 711 to 714 described as follows.

Figure 8:
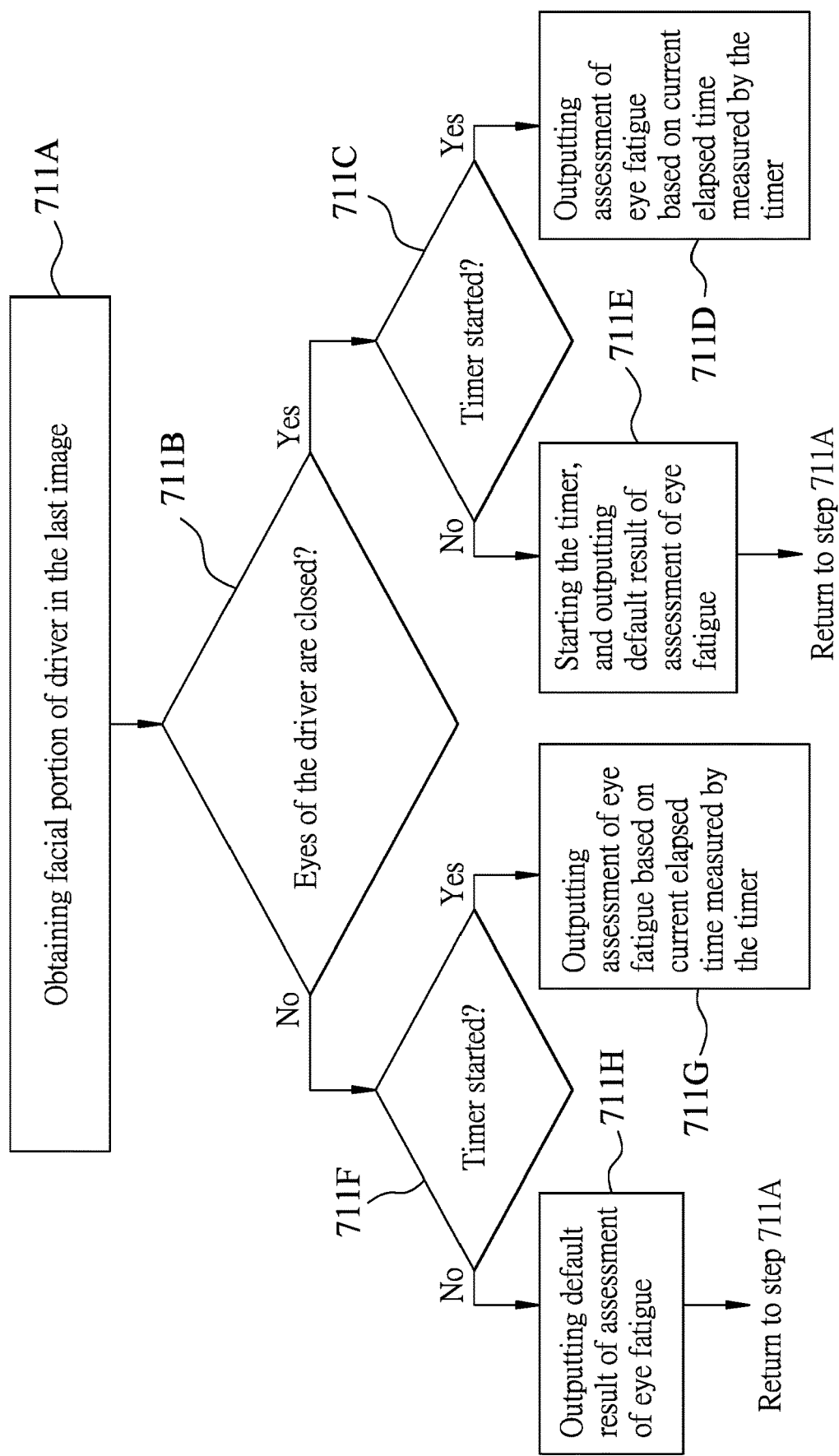
FIGS. 8 to 11 are flow charts respectively illustrating embodiments of sub-procedures of obtaining the entry of behavioral information in the method for assessing driver fatigue according to the disclosure.

In sub-step 711, based on the last one of the images of the driver captured by the image capturing device 13, the processor 15 obtains the assessment of eye fatigue of the entry of behavioral information. Specifically speaking, sub-step 711 further includes sub-steps 711A to 711H as shown in FIG. 8 and described as follows.

In sub-step 711A, based on the last one of the images of the driver captured by the image capturing device 13, the processor 15 obtains the facial portion of the driver in the last one of the images.

In sub-step 711B, the processor 15 determines whether eyes of the facial portion of the driver in the last one of the images are closed. When it is determined by the processor 15 that the eyes of the facial portion of the driver in the last one of the images are closed, a flow of procedure proceeds to sub-step 711C. On the other hand, when it is determined by the processor 15 that the eyes of the facial portion of the driver in the last one of the images are open, the flow proceeds to sub-step 711F.

In sub-step 711C, the processor 15 determines whether a timer has been started by the processor 15 for the purpose of eye fatigue assessment. When it is determined by the processor 15 that the timer has been started for the purpose of eye fatigue assessment, the flow proceeds to sub-step 711D. On the other hand, when it is determined by the processor 15 that the timer has not yet been started for the purpose of eye fatigue assessment, the flow proceeds to sub-step 711E.

In sub-step 711D, based on a current elapsed time measured by the timer, the processor 15 outputs the assessment of eye fatigue. It should be noted that in sub-step 711D, the processor 15 determines whether the current elapsed time measured by the timer is longer than a preset eyes-closed duration. When it is determined by the processor 15 that the current elapsed time measured by the timer is longer than the preset eyes-closed duration, the processor 15 outputs the assessment of eye fatigue which indicates that the eyes of the driver have a higher degree of fatigue due to a relatively longer eyes-closed duration having been measured. Oppositely, when it is determined by the processor 15 that the current elapsed time measured by the timer is not longer than the preset eyes-closed duration, the processor 15 outputs the assessment of eye fatigue which indicates that the eyes of the driver have a lower degree of fatigue.

In sub-step 711E, the processor 15 starts the timer for the purpose of eye fatigue assessment, and outputs a default result of the assessment of the eye fatigue. Then, the flow returns to sub-step 711A. It should be noted that since an input parameter to the classification model for fatigue level assessment should not be null, the default result of the assessment of the eye fatigue is utilized as the input parameter to the classification model for fatigue level assessment for further neural network computations. In this embodiment, the default result of the assessment of the eye fatigue indicates that the eyes of the driver have a lower degree of fatigue. However, in other embodiments, the default result of the assessment of the eye fatigue may indicate that the eyes of the driver have a medium degree or a higher degree of fatigue, and is not limited to the disclosure herein.

In sub-step 711F, the processor 15 determines whether the timer has been started for the purpose of eye fatigue assessment. When it is determined by the processor 15 that the timer has been started for the purpose of eye fatigue assessment, the flow proceeds to sub-step 711G. Otherwise, when it is determined by the processor 15 that the timer has not been started for the purpose of eye fatigue assessment, the flow proceeds to sub-step 711H.

In sub-step 711G, based on the current elapsed time measured by the timer, the processor 15 outputs the assessment of eye fatigue. It should be noted that in sub-step 711G, the processor 15 stops the timer at first so as to obtain a blink duration which is counted from start to stop of the timer, during which the driver had his/her eyes kept shut and at the end of which the driver opened his/her eyes. Thereafter, the processor 15 resets the timer for the purpose of eye fatigue assessment (e.g., resets the timer to zero), and obtains a blink rate that is associated with a frequency of blinking of the driver based on the blink duration. Subsequently, the processor 15 determines whether the blink rate is greater than a preset blink-rate threshold. When it is determined by the processor 15 that the blink rate is greater than the preset blink-rate threshold, the processor 15 outputs the assessment of eye fatigue which indicates that the eyes of the driver have a higher degree of fatigue. Oppositely, when it is determined by the processor 15 that the blink rate is not greater than the preset blink-rate threshold, the processor 15 outputs the assessment of eye fatigue which indicates that the eyes of the driver have a lower degree of fatigue.

In sub-step 711H, the processor 15 outputs the default result of the assessment of eye fatigue. Then, the flow returns to sub-step 711A.

Figure 9:
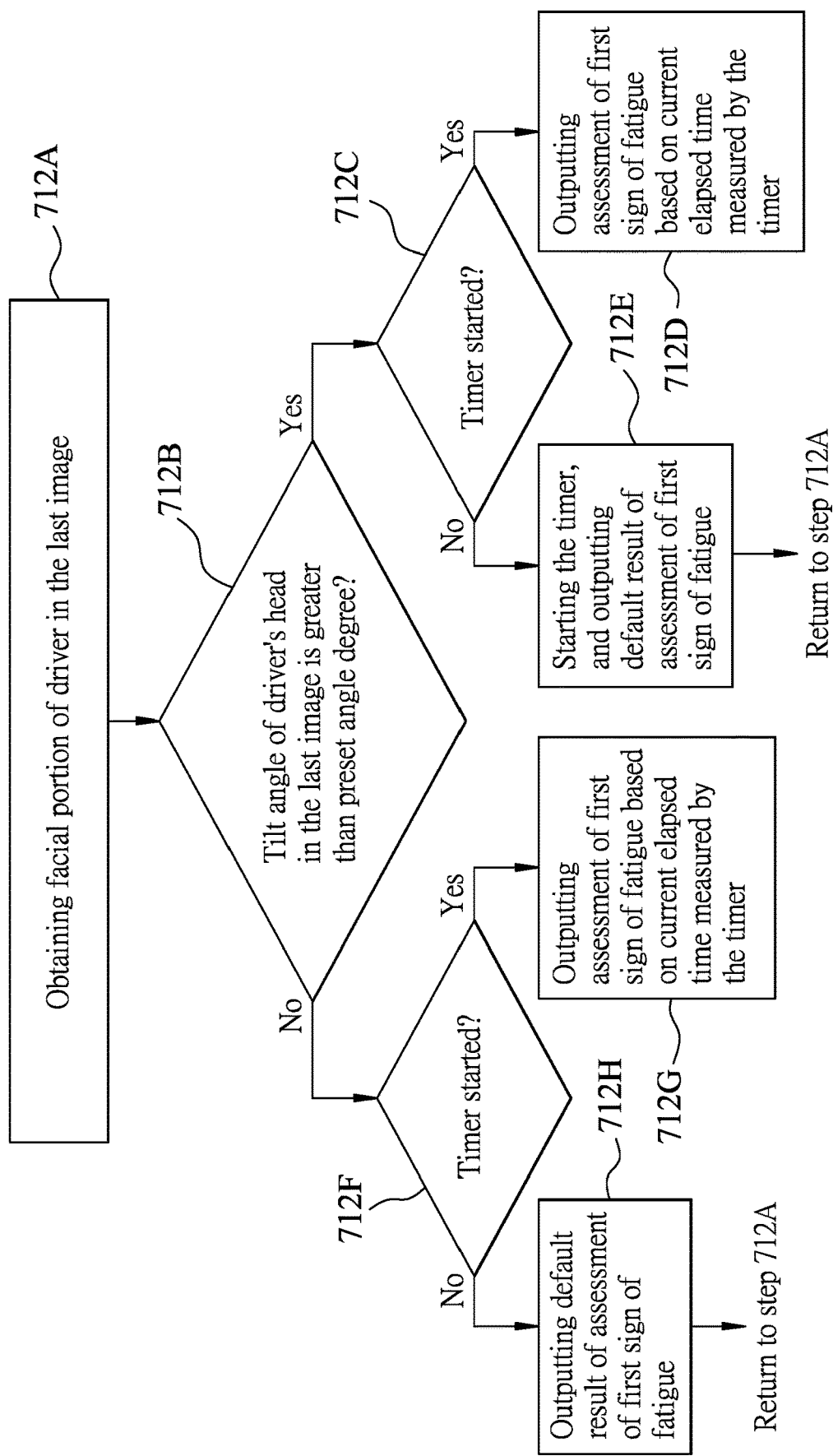

In sub-step 712, based on the last one of the images of the driver captured by the image capturing device 13, the processor 15 obtains the assessment of the first sign of fatigue of the entry of behavioral information. Specifically speaking, sub-step 712 further includes sub-steps 712A to 712H as shown in FIG. 9 and described as follows.

In sub-step 712A, based on the last one of the images of the driver captured by the image capturing device 13, the processor 15 obtains the facial portion of the driver in the last one of the images.

In sub-step 712B, the processor 15 determines whether a tilt angle that is defined by an angle at which a head of the driver is tilted relative to his/her neck in the last one of the images is greater than a preset angle degree. When it is determined by the processor 15 that the tilt angle is greater than a preset angle degree, the flow proceeds to sub-step 712C. On the other hand, when it is determined by the processor 15 that the tilt angle is not greater than the preset angle degree, the flow proceeds to sub-step 712F.

In sub-step 712C, the processor 15 determines whether the timer has been started by the processor 15 for the purpose of first sign assessment. When it is determined by the processor 15 that the timer has been started for the purpose of first sign assessment, the flow proceeds to sub-step 712D. On the other hand, when it is determined by the processor 15 that the timer has not been started for the purpose of first sign assessment, the flow proceeds to sub-step 712E.

In sub-step 712D, based on the current elapsed time measured by the timer, the processor 15 outputs the assessment of the first sign of fatigue. It should be noted that in sub-step 712D, the processor 15 determines whether the current elapsed time measured by the timer is longer than a preset head-tilt duration. When it is determined by the processor 15 that the current elapsed time measured by the timer is longer than the preset head-tilt duration, the processor 15 outputs the assessment of the first sign of fatigue which indicates that the driver has a higher degree of fatigue due to a relative longer head-tilt duration. Oppositely, when it is determined by the processor 15 that the current elapsed time measured by the timer is not longer than the preset head-bent duration, the processor 15 outputs the assessment of the first sign of fatigue which indicates that the driver has a lower degree of fatigue.

In sub-step 712E, the processor 15 starts the timer for the purpose of first sign assessment, and outputs a default result of the assessment of the first sign of fatigue. Then, the flow returns to sub-step 712A. It should be noted that since the input parameter to the classification model for fatigue level assessment should not be null, the default result of the assessment of the first sign of fatigue is utilized as the input parameter to the classification model for fatigue level assessment for further neural network computations. In this embodiment, the default result of the assessment of the first sign of fatigue indicates that the driver has a lower degree of fatigue. However, in other embodiments, the default result of the assessment of the first sign of fatigue may be implemented to indicate that the driver has a medium degree or a higher degree of fatigue, and is not limited to the disclosure herein.

In sub-step 712F, the processor 15 determines whether the timer has been started by the processor 15 for the purpose of first sign assessment. When it is determined by the processor 15 that the timer has been started for the purpose of first sign assessment, the flow proceeds to sub-step 712G. Otherwise, when it is determined by the processor 15 that the timer has not been started for the purpose of first sign assessment, the flow proceeds to sub-step 712H.

In sub-step 712G, based on the current elapsed time measured by the timer, the processor 15 outputs the assessment of the first sign of fatigue. It should be noted that in sub-step 712G, the processor 15 stops the timer for the purpose of first sign assessment at first so as to obtain a tilt duration during which the driver tilted his/her head and by the end of which returned his/her head to the normal, upright position. Thereafter, the processor 15 resets the timer (e.g., resets the timer to zero), and obtains a tilting rate that is associated with a frequency of head tilting of the driver based on the tilt duration. Subsequently, the processor 15 determines whether the tilting rate is greater than a preset tilting-rate threshold. When it is determined by the processor 15 that the tilting rate is greater than the preset tilting-rate threshold, the processor 15 outputs the assessment of the first sign of fatigue which indicates that the driver has a higher degree of fatigue. Oppositely, when it is determined by the processor 15 that the tilting rate is not greater than the preset tilting-rate threshold, the processor 15 outputs the assessment of the first sign of fatigue which indicates that the driver has a lower degree of fatigue.

In sub-step 712H, the processor 15 outputs the default result of the assessment of the first sign of fatigue. Then, the flow returns to sub-step 712A.

Figure 10:
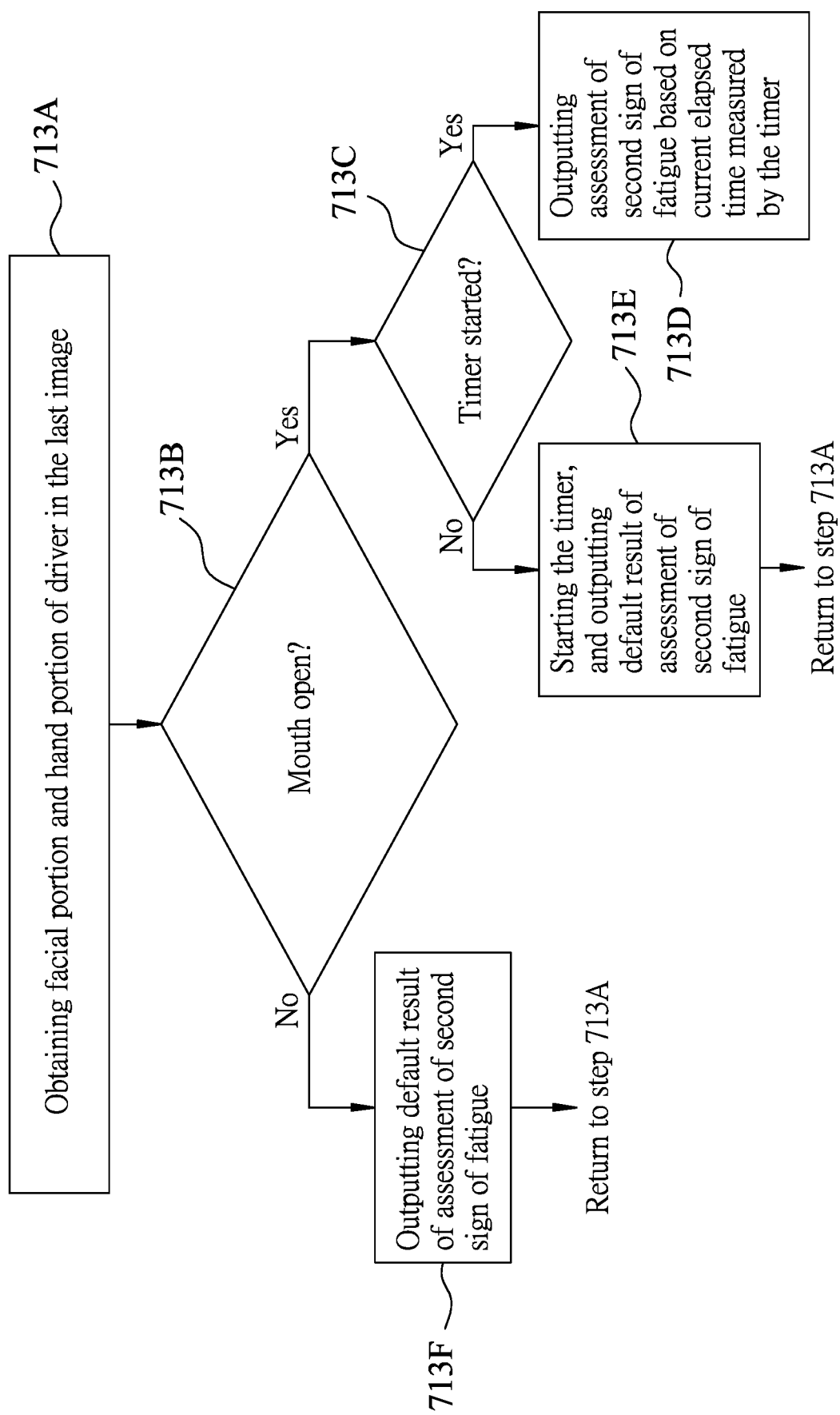

In sub-step 713, based on the last one of the images of the driver captured by the image capturing device 13, the processor 15 obtains the assessment of the second sign of fatigue of the entry of behavioral information. Specifically speaking, sub-step 713 further includes sub-steps 713A to 713F as shown in FIG. 10 and described as follows.

In sub-step 713A, based on the last one of the images of the driver captured by the image capturing device 13, the processor 15 obtains the facial portion and a hand portion of the driver in the last one of the images.

In sub-step 713B, the processor 15 determines whether a mouth of the driver is open based on whether the facial portion of the driver in the last one of the images shows that the mouth is open or whether an overlapping area between the mouth and a hand of the driver shown by the facial portion and the hand portion of the driver in the last one of the images is greater than a preset area threshold of hand-face overlap. When it is determined by the processor 15 that the mouth of the driver is open, i.e., the facial portion of the driver in the last one of the images shows that the mouth is open or the overlapping area between the mouth and the hand of the driver shown by the facial portion and the hand portion of the driver in the last one of the images is greater than the preset area threshold of hand-face overlap, the flow proceeds to sub-step 713C. On the other hand, when it is determined by the processor 15 that the mouth of the driver is not open, i.e., the facial portion of the driver in the last one of the images shows that the mouth is not open or the overlapping area between the mouth and the hand of the driver shown by the facial portion and the hand portion of the driver in the last one of the images is not greater than the preset area threshold of hand-face overlap, the flow proceeds to sub-step 713F.

In sub-step 713C, the processor 15 determines whether the timer has been started by the processor 15 for the purpose of second sign assessment. When it is determined by the processor 15 that the timer has been started for the purpose of second sign assessment, the flow proceeds to sub-step 713D. On the other hand, when it is determined by the processor 15 that the timer has not been started for the purpose of second sign assessment, the flow proceeds to sub-step 713E.

In sub-step 713D, based on the current elapsed time measured by the timer, the processor 15 outputs the assessment of the second sign of fatigue. It should be noted that in sub-step 713D, the processor 15 determines whether the current elapsed time measured by the timer is longer than a preset yawn duration. When it is determined by the processor 15 that the current elapsed time measured by the timer is longer than the preset yawn duration, the processor 15 outputs the assessment of the second sign of fatigue which indicates that the driver is yawning, and the processor 15 resets the timer (e.g., resets the timer to zero). Oppositely, when it is determined by the processor 15 that the current elapsed time measured by the timer is not longer than the preset yawn duration, the processor 15 outputs the assessment of the second sign of fatigue which indicates that the driver is not yawning.

In sub-step 713E, the processor 15 starts the timer for the purpose of second sign assessment, and outputs a default result of the assessment of the second sign of fatigue. Then, the flow returns to sub-step 713A. It should be noted that since the input parameter to the classification model for fatigue level assessment should not be null, the default result of the assessment of the second sign of fatigue is utilized as the input parameter to the classification model for fatigue level assessment for further neural network computations. In this embodiment, the default result of the assessment of the second sign of fatigue indicates that the driver is not yawning. However, in other embodiments, the default result of the assessment of the second sign of fatigue may indicate that the driver is yawning, and is not limited to the disclosure herein.

In sub-step 713F, the processor 15 outputs the default result of the assessment of the second sign of fatigue which indicates that the driver is not yawning. Then, the flow returns to sub-step 713A.

Figure 11:
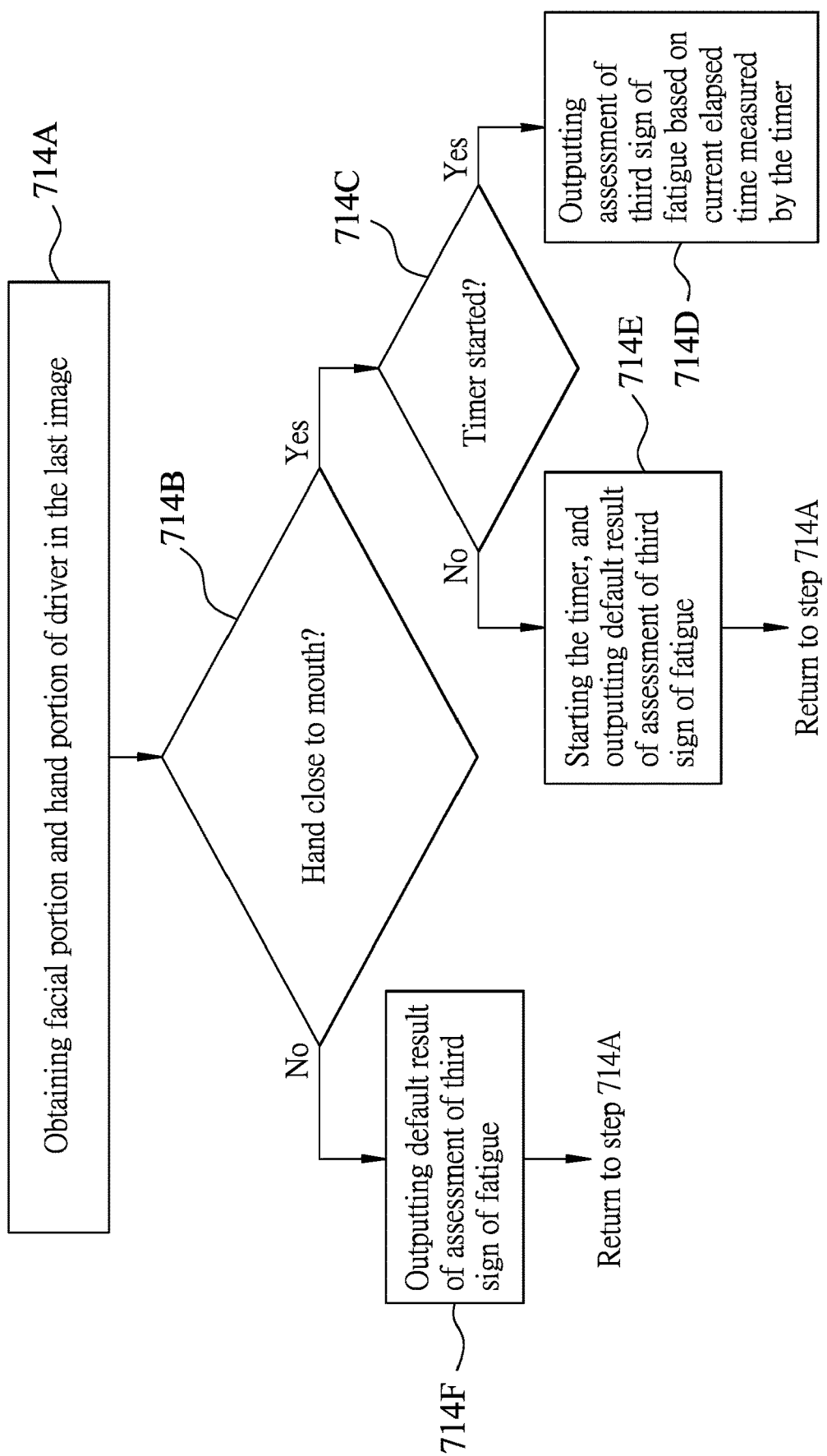

In sub-step 714, based on the last one of the images of the driver captured by the image capturing device 13, the processor 15 obtains the assessment of the third sign of fatigue of the entry of behavioral information. Specifically speaking, sub-step 714 further includes sub-steps 714A to 714F as shown in FIG. 11 and described as follows.

In sub-step 714A, based on the last one of the images of the driver captured by the image capturing device 13, the processor 15 obtains the facial portion and the hand portion of the driver in the last one of the images.

In sub-step 714B, the processor 15 determines whether the hand of the driver is close to or nearby his/her eyes by determining whether an overlapping area between the eyes and the hand of the driver shown by the facial portion and the hand portion of the driver in the last one of the images is greater than a preset area threshold of hand-eyes overlap. When it is determined by the processor 15 that the hand of the driver is close to his/her eyes, i.e., the overlapping area between the eyes and the hand of the driver shown by the facial portion and the hand portion of the driver in the last one of the images is greater than the preset area threshold of hand-eyes overlap, the flow proceeds to sub-step 714C. On the other hand, when it is determined by the processor 15 that the hand of the driver is not close to his/her eyes, i.e., the overlapping area between the eyes and the hand of the driver shown by the facial portion and the hand portion of the driver in the last one of the images is not greater than the preset area threshold of hand-eyes overlap, the flow proceeds to sub-step 714F.

In sub-step 714C, the processor 15 determines whether the timer has been started by the processor 15 for the purpose of third sign assessment. When it is determined by the processor 15 that the timer has been started for the purpose of third sign assessment, the flow proceeds to sub-step 714D. On the other hand, when it is determined by the processor 15 that the timer has not been started for the purpose of third sign assessment, the flow proceeds to sub-step 714E.

In sub-step 714D, based on the current elapsed time measured by the timer, the processor 15 outputs the assessment of the third sign of fatigue. It should be noted that in sub-step 714D, the processor 15 determines whether the current elapsed time measured by the timer is longer than a preset eye-rubbing duration. When it is determined by the processor 15 that the current elapsed time measured by the timer is longer than the preset eye-rubbing duration, the processor 15 outputs the assessment of the third sign of fatigue which indicates that the driver is rubbing his/her eye(s), and the processor 15 resets the timer (e.g., resets the timer to zero). Oppositely, when it is determined by the processor 15 that the current elapsed time measured by the timer is not longer than the preset eye-rubbing duration, the processor 15 outputs the assessment of the third sign of fatigue which indicates that the driver is not rubbing his/her eyes.

In sub-step 714E, the processor 15 starts the timer for the purpose of third sign assessment, and outputs a default result of the assessment of the third sign of fatigue. Then, the flow returns to sub-step 714A. It should be noted that since the input parameter to the classification model for fatigue level assessment should not be null, the default result of the assessment of the third sign of fatigue is utilized as the input parameter to the classification model for fatigue level assessment for further neural network computations. In this embodiment, the default result of the assessment of the third sign of fatigue indicates that the driver is not rubbing his/her eyes. However, in other embodiments, the default result of the assessment of the third sign of fatigue may indicate that the driver is rubbing his/her eye(s), and is not limited to the disclosure herein.

In sub-step 714F, the processor 15 outputs the default result of the assessment of the third sign of fatigue which indicates that the driver is not rubbing his/her eyes. Then, the flow returns to sub-step 714A.

One of ordinary skill in the art should appreciate that steps 711 to 714 do not have to be performed in the sequential manner as illustrated in FIG. 7, and may be performed in parallel or in any other order, as design requires, as long as the instances of timing started for the different types of assessment are not mixed up.

Figure 12:
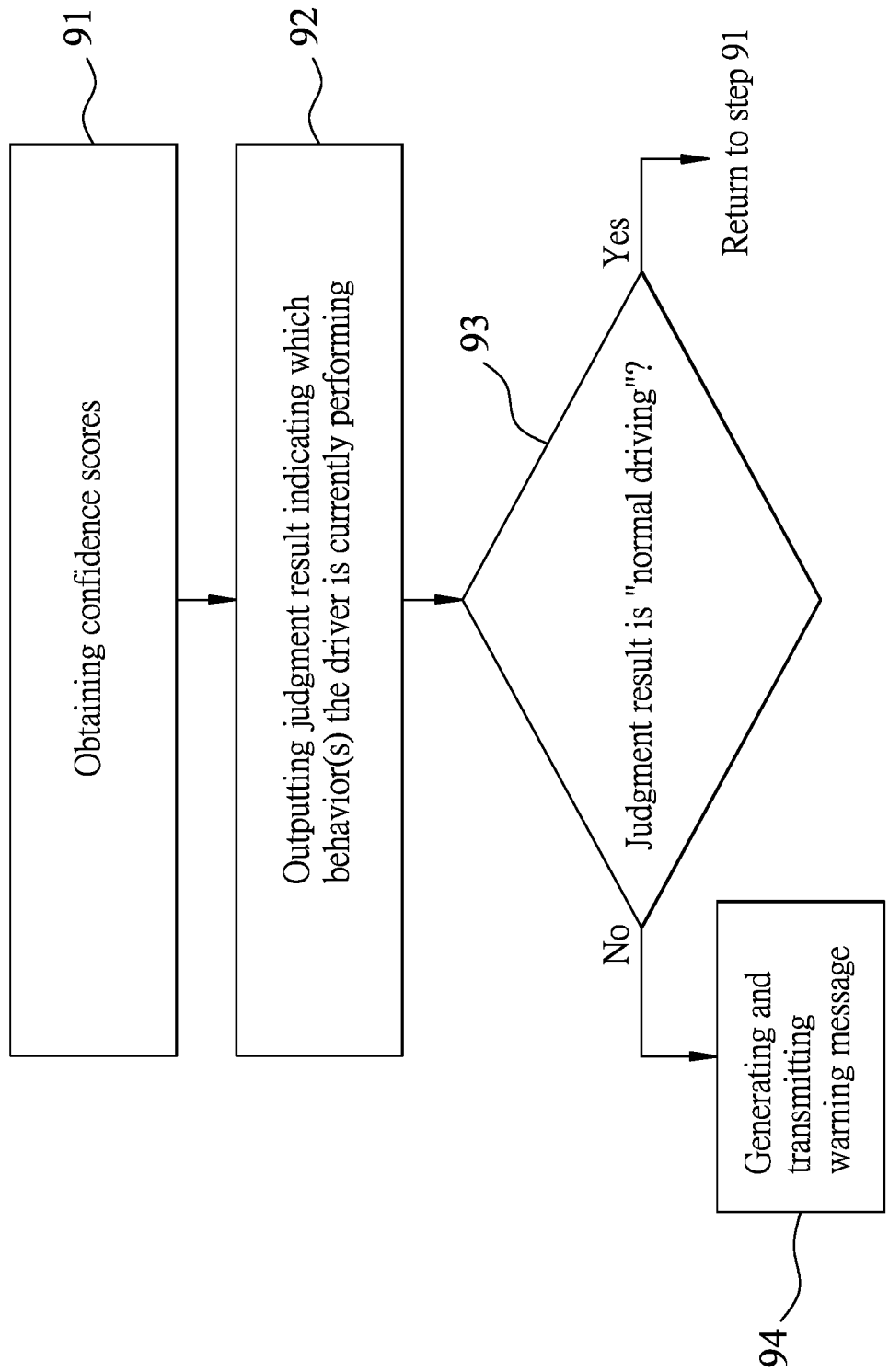
FIG. 12 is a flow chart illustrating an embodiment of a procedure of warning the driver in the method for assessing driver fatigue according to the disclosure.

Referring to FIG. 12, the procedure of warning the driver is illustrated. The processor 15 determines whether the driver might be driving inappropriately according to the last one of the images of the driver captured by the image capturing device 13, and generates another warning message to warn the driver when it is determined that the driver might be driving inappropriately. The procedure of warning the driver includes steps 91 to 94 described as follows.

In step 91, for each of the images of the driver captured by the image capturing device 13, based on the predetermined classification model of driver behavior, the processor 15 performs an algorithm of neural network on the image so as to obtain a plurality of confidence scores. The confidence scores respectively correspond to different behaviors of the driver. In this embodiment, the behaviors of the driver exemplarily include "normal driving", "using a mobile", "eating and/or drinking", and "turning around to get something". However, the behaviors of the driver corresponding to the confidence scores are not limited to the disclosure herein and may vary in other embodiments.

In step 92, for each of the confidence scores, the processor 15 calculates a variation in the confidence score among the images of the driver captured in a predetermined time period, and determines whether the variation in the confidence score is greater than a variation threshold. When it is determined that the variation in one of the confidence scores is greater than the variation threshold, the processor 15 outputs a judgment result indicating which one of the behaviors the driver is currently performing, where said one of the behaviors indicated by the judgment result corresponds to said one of the confidence scores. It should be noted that the judgment result may include more than one of the behaviors of the driver when variations in more than one of the confidence scores are greater than the variation threshold.

In step 93, the processor 15 determines whether the judgment result is "normal driving". When it is determined by the processor 15 that the judgment result is "normal driving", the flow returns to step 91. Otherwise, when it is determined by the processor 15 that the judgment result is not "normal driving", the flow proceeds to step 94. Generally speaking, if all behaviors of the driver corresponding to the confidence scores other than "normal driving", such as "using a mobile", "eating and/or drinking", and "turning around to get something", are considered "abnormal driving", then a judgment result that includes "normal driving" would normally not also include other behaviors, and so this type of judgment result includes only one of the behaviors of the driver, that is, the "normal driving" behavior. On the other hand, a judgment result that is not "normal driving" may include one or more of the "abnormal driving" behaviors.

In step 94, the processor 15 generates said another warning message and transmits said another warning message to the warning module 14 to ask the driver to concentrate on driving.

In summary, the method for assessing driver fatigue according to the disclosure utilizes the processor 15 to obtain the fatigue score that indicates the level of fatigue of the driver by using, based on the entry of physiological information, the entry of facial expression information and the entry of behavioral information, the classification model for fatigue level assessment that is trained with algorithms of neural networks. Consequently, condition of the driver can be determined based on the fatigue score. Moreover, the entry of behavioral information thus obtained based on the images of the driver can be utilized by the processor to determine whether the driver is currently conducting inappropriate driving behaviors, such as using a mobile phone while driving, and to notify the driver of the need to drive properly, reducing the risk of driving and improving traffic safety.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for assessing driver fatigue, to be implemented by a processor, the processor being electrically connected to an image capturing device, the image capturing device continuously capturing a plurality of images of a driver, the method comprising:
   (A) based on the images of the driver captured by the image capturing device, obtaining an entry of physiological information that indicates a physiological state of the driver;
   (B) based on one of the images of the driver, obtaining an entry of facial expression information that indicates an emotional state of the driver;
   (C) based on one of the images of the driver, obtaining an entry of behavioral information that indicates driver behavior of the driver; and
   (D) based on the entry of physiological information, the entry of facial expression information and the entry of behavioral information, obtaining a fatigue score that indicates a level of fatigue of the driver,
   wherein the entry of physiological information is in frequency domain,
   wherein step (A) includes sub-steps of:
   (A-1') for each of the images, based on the image, obtaining a facial sub-image that corresponds to a facial region of the driver in the image,
   (A-2') based on the facial sub-images for the images, obtaining a time-domain waveform that is associated with heartbeat of the driver, and
   (A-3') based on the time-domain waveform and by using Fourier transform, obtaining a ratio of low frequency to high frequency power (LF/HF ratio) that is associated with sympathovagal balance of the driver and that is included in the entry of physiological information.

2. The method as claimed in claim 1, wherein step (A-2') includes sub-steps of:
   (A-2'-1) based on the facial sub-images for the images, obtaining a photoplethysmography (PPG) signal; and
   (A-2'-2) based on the PPG signal, obtaining the time-domain waveform.

3. The method as claimed in claim 1, wherein step (D) includes sub-steps of:
   (D-1') based on the LF/HF ratio of the entry of physiological information and a fuzzy model that is associated with LF/HF ratio, obtaining an LF/HF-ratio score that is associated with the driver; and
   (D-2') obtaining the fatigue score that indicates the level of fatigue of the driver based on the LF/HF-ratio score by using a classification model for fatigue level assessment that is associated with LF/HF ratio, facial expression information and behavioral information.

4. The method as claimed in claim 1, wherein step (B) includes sub-steps of:
   (B-1) based on a last one of the images of the driver captured by the image capturing device, obtaining a facial portion of the driver in the last one of the images; and
   (B-2) based on the facial portion of the driver in the last one of the images by using a predetermined classification model of facial expression, obtaining the entry of facial expression information that corresponds to the facial expression of the driver in the last one of the images and that includes an anger score, a disgust score, a scare score, a happiness score, a sadness score and an amazement score.

5. A method for assessing driver fatigue, to be implemented by a processor, the processor being electrically connected to an image capturing device, the image capturing device continuously capturing a plurality of images of a driver, the method comprising:
- (A) based on the images of the driver captured by the image capturing device, obtaining an entry of physiological information that indicates a physiological state of the driver;
- (B) based on one of the images of the driver, obtaining an entry of facial expression information that indicates an emotional state of the driver;
- (C) based on one of the images of the driver, obtaining an entry of behavioral information that indicates driver behavior of the driver; and
- (D) based on the entry of physiological information, the entry of facial expression information and the entry of behavioral information, obtaining a fatigue score that indicates a level of fatigue of the driver, wherein the entry of physiological information is in time domain, wherein step (A) includes sub-steps of:
- (A-1) for each of the images, based on the image, obtaining a facial sub-image that corresponds to a facial region of the driver in the image,
- (A-2) based on the facial sub-images for the images, obtaining a time-domain waveform that is associated with heartbeat of the driver, and
- (A-3) based on the time-domain waveform, obtaining a heart rate that is a number of heartbeats of the driver per unit of time and that is included in the entry of physiological information, and a standard deviation of normal-to-normal intervals (SDNN) that is associated with the heartbeat of the driver and that is included in the entry of physiological information, wherein step (D) includes sub-steps of:
- (D-1) based on the heart rate of the entry of physiological information and a fuzzy model that is associated with heart rate, obtaining a heart-rate score that is associated with the driver,
- (D-2) based on the SDNN of the entry of physiological information and a fuzzy model that is associated with SDNN, obtaining an SDNN score that is associated with the driver, and
- (D-3) obtaining the fatigue score that indicates the level of fatigue of the driver based on the heart-rate score and the SDNN score by using a classification model for fatigue level assessment that is associated with heart rate, SDNN, facial expression information and behavioral information.

6. The method as claimed in claim 5, wherein step (A-2) includes sub-steps of:
- (A-2-1) based on the facial sub-images for the images, obtaining a photoplethysmography (PPG) signal; and
- (A-2-2) based on the PPG signal, obtaining the time-domain waveform.

\* \* \* \* \*